US011567088B2

(12) United States Patent
LaBaer et al.

(10) Patent No.: US 11,567,088 B2
(45) Date of Patent: Jan. 31, 2023

(54) METHODS FOR DIAGNOSIS OF TYPE 1 DIABETES

(71) Applicants: Joshua LaBaer, Chandler, AZ (US); Ji Qiu, Chandler, AZ (US); Xiaofang Bian, Mesa, AZ (US); Desmond A. Schatz, Gainesville, FL (US); Clive H. Wasserfall, Gainesville, FL (US); Mark A. Atkinson, Gainesville, FL (US)

(72) Inventors: Joshua LaBaer, Chandler, AZ (US); Ji Qiu, Chandler, AZ (US); Xiaofang Bian, Mesa, AZ (US); Desmond A. Schatz, Gainesville, FL (US); Clive H. Wasserfall, Gainesville, FL (US); Mark A. Atkinson, Gainesville, FL (US)

(73) Assignees: ARIZONA BOARD OF REGENTS ON BEHALF OF ARIZONA STATE UNIVERSITY, Scottsdale, AZ (US); UNIVERSITY OF FLORIDA RESEARCH FOUNDATION INC., Gainesville, FL (US)

( * ) Notice: Subject to any disclaimer, the term of this patent is extended or adjusted under 35 U.S.C. 154(b) by 0 days.

(21) Appl. No.: 16/791,640

(22) Filed: Feb. 14, 2020

(65) Prior Publication Data

US 2020/0182887 A1 Jun. 11, 2020

Related U.S. Application Data

(63) Continuation of application No. 14/990,504, filed on Jan. 7, 2016, now abandoned.

(60) Provisional application No. 62/100,775, filed on Jan. 7, 2015.

(51) Int. Cl.
*G01N 33/00* (2006.01)
*G01N 33/68* (2006.01)
*G01N 33/564* (2006.01)

(52) U.S. Cl.
CPC ....... *G01N 33/6893* (2013.01); *G01N 33/564* (2013.01); *G01N 2800/042* (2013.01); *G01N 2800/50* (2013.01)

(58) Field of Classification Search
None
See application file for complete search history.

(56) References Cited

U.S. PATENT DOCUMENTS

2010/0266610 A1  10/2010  Zmuda

FOREIGN PATENT DOCUMENTS

EP   1360490 B1   11/2003
WO  2008061104 A2   5/2008

OTHER PUBLICATIONS

Achenbach et al., Characteristics of rapid vs slow progression to type 1 diabetes in multiple islet autoantibody-positive children., Diabetologia, Jul. 2013, 56(7):1615-1622.
Achenbach et al., Stratification of Type 1 Diabetes Risk on the Basis of Islet Autoantibody Characteristics., Diabetes, Feb. 2004, 53(2):384-392.
Arden et al., Molecular cloning of a pancreatic islet-specific glucose-6-phosphatase catalytic subunit-related protein., Diabetes, 1999, 48(3):531-542.
Atkinson, The pathogenesis and natural history of type 1 diabetes., Cold Spring Harbor Perspectives in Medicine, Nov. 2012, 2(11):a007641.
Baekkeskov et al., Identification of the 64K autoantigen in insulin-dependent diabetes as the GABA-synthesizing enzyme glutamic acid decarboxylase., Nature, Sep. 1990, 347(6289):151-156.
Bian et al., Antiviral antibody profiling by high-density protein arrays., Proteomics, Jun. 2015, 15(12):2136-2145.
Bian et al., Immunoproteomic Profiling of Anti-Viral Antibodies in New-Onset Type 1 Diabetes Using Protein Arrays., Diabetes, 2016, 65(1):285-96.
Bonifacio et al., Identification of protein tyrosine phosphatase-like IA2 (islet cell antigen 512) as the insulin-dependent diabetes-related 37/40K autoantigen and a target of islet-cell antibodies., The Journal of Immunology, Dec. 1995, 155(11):5419-5426.
Bronner et al., Mutation in the DNA mismatch repair gene homologue hMLH1 is associated with hereditary non-polyposis colon cancer., Nature, Mar. 1994, 368(6468):258-261.
De Graeff-Meeder et al., Antibodies to human HSP60 in patients with juvenile chronic arthritis, diabetes mellitus, and cystic fibrosis., Pediatric Research, 1993, 34(4):424-428.
Eizirik et al., The role of inflammation in insulitis and ?-cell loss in type 1 diabetes., The role of inflammation in insulitis and ?-cell loss in type 1 diabetes, Apr. 2009, 5(4):219-226.
Eringsmark Regnell et al., The environment and the origins of islet autoimmunity and Type 1 diabetes., Diabetic Medicine, Feb. 2013, 30(2):155-160.
Festa et al., High-throughput cloning and expression library creation for functional proteomics., Proteomics, May 2013, 13(9):1381-1399.
Festa et al., Robust microarray production of freshly expressed proteins in a human milieu., Proteomics—Clinical Applications, Jun. 2013, 7(5-6):372-377.
Fonseca et al., Endoplasmic reticulum stress in ß-cells and development of diabetes., Current Opinion in Pharmacology, Dec. 2009, 9(6):763-770.

(Continued)

*Primary Examiner* — G. R. Ewoldt
(74) *Attorney, Agent, or Firm* — Quarles & Brady, LLP

(57) ABSTRACT

Type 1 diabetes (T1D) patients make antibodies to self-proteins that are potential biomarkers for early detection and risk prediction. We have identified seventeen antigens as biomarkers for early diagnosis and risk prediction of T1D, including the antigens MLH1, MTIF3, PPIL2, NUP50, TOX4, FIGN, C9orf142, ZNF280D, HES1, QRFPR, CTRC, SNX6, SYTL4, ELA2A, IGRP, PAX6, and HMGN3.

6 Claims, 1 Drawing Sheet

(56) References Cited

OTHER PUBLICATIONS

Goumidi et al., Effects of established BMI-associated loci on obesity-related traits in a French representative population sample., BMC Genetics, May 2014, 15(1):62(5 pages).

Granata et al., RFamide Peptides 43RFa and 26RFa Both Promote Survival of Pancreatic beta-Cells and Human Pancreatic Islets but Exert Opposite Effects on Insulin Secretion., Diabetes, Jul. 2014, 63(7):2380-2393.

Hirai et al., Selective screening of secretory vesicle-associated proteins for autoantigens in type 1 diabetes: VAMP2 and NPY are new minor autoantigens., Clinical Immunology, Jun. 2008,127(3):366-374.

Jacobsson et al., Identification of Synaptic Proteins and Their Isoform mRNAs in Compartments of Pancreatic Endocrine Cells., Proceedings of the National Academy of Sciences of the United States of America, Dec. 1994, 91(26):12487-12491.

Kasimiotis et al., Sex-determining region Y-related protein SOX13 is a diabetes autoantigen expressed in pancreatic islets., Diabetes, Apr. 2000, 49(4):555-561.

Kawasaki et al., Molecular Cloning and Characterization of the Human Transmembrane Protein Tyrosine Phosphatase Homologue, Phogrin, an Autoantigen of Type 1 Diabetes., Biochemical and Biophysical Research Communications, Oct. 1996, 227(2):440-447.

Koo et al., Identification of Novel Autoantibodies in Type 1 Diabetic Patients Using a High-Density Protein Microarray., Diabetes, Sep. 2014, 63(9):3022-3032.

Larman et al., PhIP-Seq characterization of autoantibodies from patients with multiple sclerosis, type 1 diabetes and rheumatoid arthritis, Journal of Autoimmunity, Jun. 2013, 43:1-9.

Lieberman et al., Identification of the ß Cell Antigen Targeted by a Prevalent Population of Pathogenic CD8+T Cells in Autoimmune Diabetes., Proceedings of the National Academy of Sciences of the United States of America, Jul. 2003, 100(14):8384-8388.

Lindskog et al., Novel pancreatic beta cell-specific proteins: Antibody-based proteomics for identification of new biomarker candidates., Journal of Proteomics, May 2012, 75(9):2611-2620.

Lu et al., Identification of a Second Transmembrane Protein Tyrosine Phosphatase, IA-2ß, as an Autoantigen in Insulin-Dependent Diabetes Mellitus: Precursor of the 37-kDa Tryptic Fragment., Proceedings of the National Academy of Sciences of the United States of America, Mar. 1996, 93(6):2307-2311.

Marino et al., B cell-directed therapies in type 1 diabetes., Trends in Immunology, Jun. 2011, 32(6):287-294.

Massa et al., Serological Proteome Analysis (SERPA) as a tool for the identification of new candidate autoantigens in type 1 diabetes, Journal of Proteomics, Apr. 2013, 82:263-273.

Miersch et al., Nucleic Acid programmable protein arrays: versatile tools for array-based functional protein studies, Current Protocols in Protein Science, Apr. 2011, Chapter 27, Unit 27.2 (26 pages).

Miersch et al., Serological autoantibody profiling of type 1 diabetes by protein arrays., Journal of Proteomics, Dec. 2013, 94:486-496.

Onkamo et al., Worldwide increase in incidence of Type I diabetes—the analysis of the data on published incidence trends., Diabetologia, Dec. 1999, 42(12):1395-1403.

Palmer et al., Insulin-Antibodies in Insulin-Dependent Diabetics before Insulin-Treatment., Science, Dec. 1983, 222 (4630):1337-1339.

Pietropaolo et al., Islet cell autoantigen 69 kD (ICA69): Molecular cloning and characterization of a novel diabetes-associated autoantigen., Journal of Clinical Investigation, Jul. 1993, 92(1):359-371.

Ramachandran et al., Next-generation high-density self-assembling functional protein arrays., Nature Methods, Jun. 2008, 5(6):535-538.

Seiler et al., DNASU plasmid and PSI: Biology-Materials repositories: resources to accelerate biological research., Nucleic Acids Research, Jan. 2014, 42(D1):D1253-D1260.

Wang et al., Plasma Autoantibodies Associated with Basal-like Breast Cancers., Cancer Epidemiology Biomarkers & Prevention, Sep. 2015, 24(9):1332-1340.

Wang et al., Prevalence of autoantibody-negative diabetes is not rare at all ages and increases with older age and obesity., Journal of Clinical Endocrinology and Metabolism, Jan. 2007, 92(1):88-92.

Wenzlau et al., The Cation Efflux Transporter ZnT8 (Slc30A8) Is a Major Autoantigen in Human Type 1 Diabetes., Proceedings of the National Academy of Sciences of the United States of America, Oct. 2007, 104(43):17040-17045.

Winnock et al., Autoantibodies to a 38-kDa glycosylated islet cell membrane-associated antigen in (pre)type 1 diabetes: Association with IA-2 and islet cell autoantibodies., Diabetes Care, Jul. 2001, 24(7):1181-1186.

Winter et al., Autoimmune markers in diabetes., Clinical Chemistry, Feb. 2011, 57(2):168-175.

"Ayachi and Simonin""Involvement of mammalian RF-amide peptides and their receptors in the modulation of nociception in rodents""Front Endocrinol (Lausanne). 2014; 5: 158."

Baumann K. "Beyond pores" Nature Reviews Molecular Cell Biology vol. 11, p. 163 (2010).

Behrouz et al. "Mitochondrial translation initiation factor 3 polymorphism and Parkinson's disease" Neurosci Lett. Dec. 17, 2010;486(3):228-30.

Brown et al. "Genome-Wide Association Study of *Staphylococcus aureus* Carriage in a Community-Based Sample of Mexican-Americans in Starr County, Texas" PLoS One. Nov. 16, 2015;10(11):e0142130.

Carson et al. "Variation in RTN3 and PPIL2 genes does not influence platelet membrane beta-secretase activity or susceptibility to alzheimer's disease in the northern Irish population" Neuromolecular Med. 2009;11(4):337-44.

Chekmareva et al. "Environmental manipulations generate bidirectional shifts in both behavior and gene regulation in a crossbred mouse model of extremes in trait anxiety" Front Behav Neurosci. Mar. 18, 2014;8:87.

Gonzalez-Granado et al. "Sorting Nexin 6 Enhances Lamin A Synthesis and Incorporation into the Nuclear Envelope" PLoS One. Dec. 23, 2014;9(12):e115571.

Manlong et al. "A new small supernumerary marker chromosome involving 14pter → q12 in a child with severe neurodevelopmental retardation: case report and literature review" Gene. Dec. 1, 2013;531(2):457-61.

Mukherjee et al. "Human Fidgetin is a microtubule severing the enzyme and minus-end depolymerase that regulates mitosis" Cell Cycle. Jun. 15, 2012; 11(12): 2359-2366.

Nemoda and Sahin-Toth "Chymotrypsin C (Caldecrin) Stimulates Autoactivation of Human Catonic Trypsinogen" J Biol Chem. Apr. 28, 2006;281(17):11879-86.

Ochi et al. "DNA repair. PAXX, a paralog of XRCC4 and XLF, interacts with Ku to promote DNA double-strand break repair" Science. Jan. 9, 2015;347(6218):185-188.

Ostrowski et al. "Rab27a and Rab27b control different steps of the exosome secretion pathway" Nat Cell Biol. Jan. 2010;12(1):19-30; sup pp. 1-13.

Petrolonis et al. "Enzymatic Characterization of the Pancreatic Islet-specific Glucose-6-Phosphatase-related Protein (IGRP)" J Biol Chem. Apr. 2, 2004;279(14):13976-83.

Quattrocelli et al. "Notch signaling regulates myogenic regenerative capacity of murine and human mesoangioblasts" Cell Death & Disease vol. 5, p. e1448 (2014).

Sengupta et al. "Inactivation of human mutL homolog 1 and mutS homolog 2 genes in head and neck squamous cell carcinoma tumors and leukoplakia samples by promoter hypermethylation and its relation with microsatellite instability phenotype" Cancer. Feb. 15, 2007;109(4):703-12.

Wen et al. "Paired box 6 (PAX6) regulates glucose metabolism via proinsulin processing mediated by prohormone convertase 1/3 (PC1/3)" Diabetologia. Mar. 2009;52(3):504-13.

Zhou and Sahin-Toth "Chymotrypsin C mutations in chronic pancreatitis" J Gastroenterol Hepatol. Aug. 2011;26(8):1238-46.

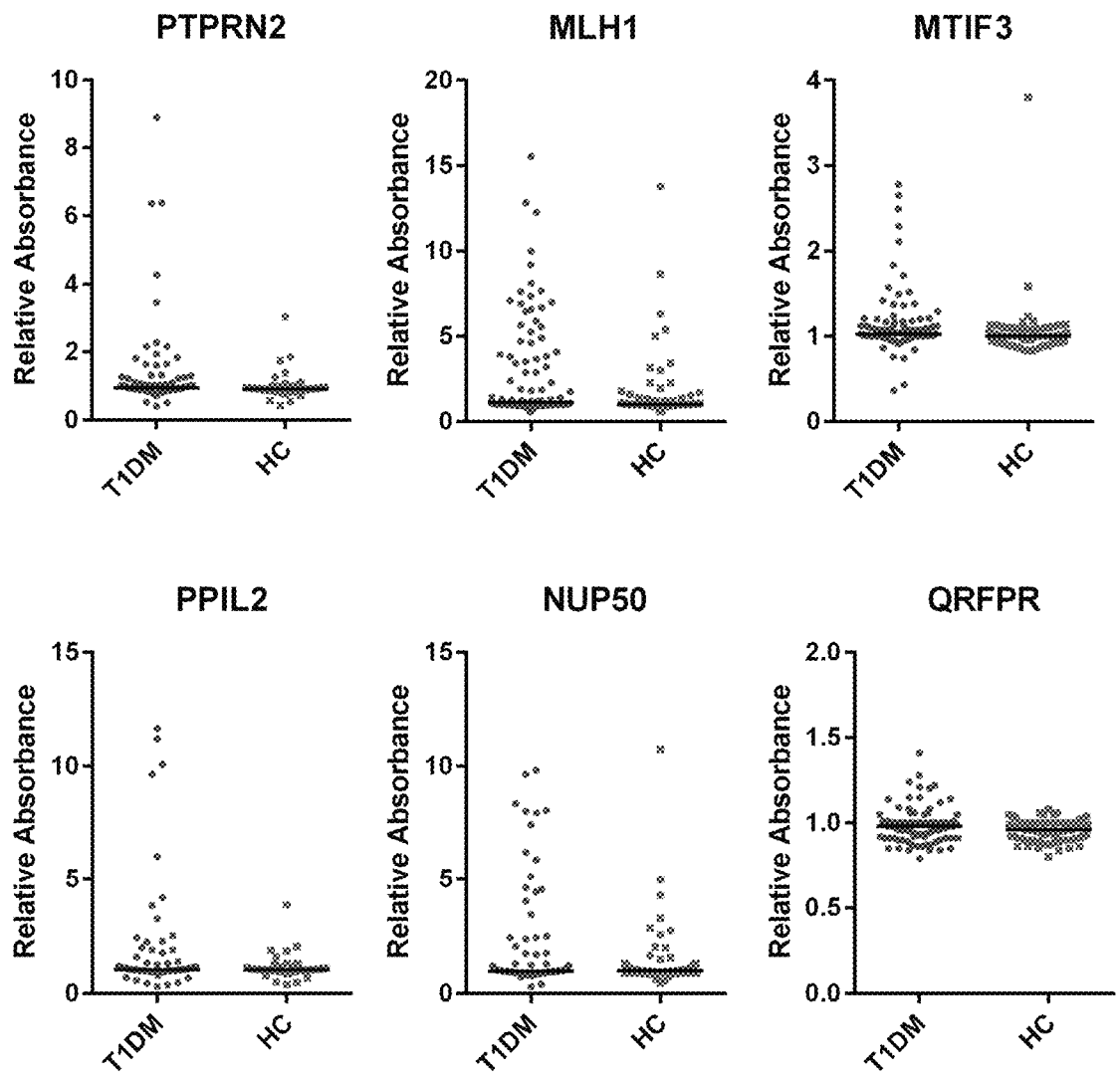

METHODS FOR DIAGNOSIS OF TYPE 1 DIABETES

CROSS-REFERENCE TO RELATED APPLICATIONS

This application is a continuation of U.S. patent application Ser. No. 14/990,504, filed Jan. 7, 2016, which claims priority to U.S. Provisional Patent Application No. 62/100,775, filed Jan. 7, 2015, each of which is incorporated herein by reference as if set forth in its entirety.

FIELD OF THE INVENTION

This disclosure relates to biomarkers for the prediction of type 1 diabetes (T1D) onset and for diagnosing T1D.

BACKGROUND OF THE INVENTION

T1D is one of the most common juvenile autoimmune diseases. It is characterized by progressive autoimmune destruction of pancreatic beta cells. The incidence of T1D is increasing worldwide. T1D patients are dependent on lifelong exogenous insulin but this is not a cure and in the long term there are serious co-morbidities. This leads to both personal and societal burdens in terms of financial and quality of life indicators. At the time of T1D diagnosis, it is thought that potentially 70%-90% of pancreatic beta cells have been destroyed. Therefore early diagnostic and prognostic markers of T1D prior to symptomatic disease onset will be of great value in identifying individuals that could benefit from intervention protocols while significant beta cell function still exists.

Prevention of T1D will only be possible if individuals with high risk for progression to T1D can be identified. The incidence of T1D in general population is around 22/100,000 in the US. The majority of T1D cases are diagnosed in non-relatives with 85% of new T1D cases occurring in individuals with no known family history. Thus, biomarkers are needed to improve our prediction models and enable the selection of subjects with, for example, high 5-year risk of disease onset. Such markers could be deployed immediately to identify high-risk subjects for intervention trials. Additionally in differentiating type 1 diabetes from other forms of diabetes mellitus autoantibodies are helpful and yet there are still some individuals with T1D that are negative for the current known autoantibodies, thus the discovery of additional autoantibodies aids in the differential diagnosis of T1D.

SUMMARY OF THE INVENTION

Identifying markers that present prior to the development of our currently used autoantibodies (AAbs) could improve the risk prediction models. Thus, the embodiments disclosed herein relate to the identification of AAb biomarkers in T1D so as to increase the sensitivity of detection in T1D patients and improve the T1D risk prediction model.

All references disclosed throughout are hereby incorporated herein in their entirety.

In one embodiment, we used a novel protein microarray technology termed "Nucleic Acid Programmable Protein Array" (NAPPA) (see, e.g., EP 1360490B1). This innovative protein microarray format avoids the need to express and purify the proteins by substituting the printing of full length cDNAs on the arrays. Proteins corresponding to the cDNAs are produced in situ as needed at the time of the assay by in vitro transcription and translation (IVTT)-coupled cell lysates. The cDNAs are configured to append a common epitope tag to all of the proteins on their C-termini so that they can be captured by a high-affinity capture reagent that is immobilized along with the cDNA.

In another embodiment, a method of diagnosing type 1 diabetes onset includes the step of contacting an antibody-containing fluid sample from a subject with one or more of antigens selected from the group consisting of MLH1, MTIF3, PPIL2, NUP50, TOX4, FIGN, C9orf142, ZNF280D, HES1, QRFPR, CTRC, SNX6, SYTL4, ELA2A, IGRP, PAX6, and HMGN3, wherein detection of antibodies with a suitable detection agent to one or more of these antigens indicates a diagnosis of type 1 diabetes onset in comparison to a healthy control sample.

In a further embodiment, a method of screening for a risk factor associated with type 1 diabetes onset includes the step of contacting an antibody-containing fluid sample from a subject with one or more antigens selected from the group consisting of MLH1, MTIF3, PPIL2, NUP50, TOX4, FIGN, C9orf142, ZNF280D, HES1, QRFPR, CTRC, SNX6, SYTL4, ELA2A, IGRP, PAX6, and HMGN3, wherein detection of antibodies with a suitable detection agent to one or more of these antigens indicates an elevated risk of type 1 diabetes onset in comparison to a healthy control sample.

These and other aspects of the embodiments disclosed herein will be apparent upon reference to the following disclosure.

BRIEF DESCRIPTION OF THE DRAWINGS

FIG. 1 depicts jitter plots of representative autoantigens from screening and knowledge based approaches (T1D stands for new-onset T1D patients; HC stands for healthy controls).

DETAILED DESCRIPTION OF THE INVENTION

The embodiments disclosed herein relate to 17 antigens that have been identified as biomarkers for early detection and risk prediction of T1D. These antigens are: MLH1, MTIF3, PPIL2, NUP50, TOX4, FIGN, C9orf142, ZNF280D, HES1, QRFPR, CTRC, SNX6, SYTL4, ELA2A, IGRP, PAX6, and HMGN3.

In general, two approaches were used to discover the disclosed antigens: a screen based approach and a knowledge based approach. To profile the serological antibody response, 40 T1D patients and 40 age/gender matched healthy controls were screened against 10,000 human proteins across 5 NAPPA array sets.

40 antigens were chosen for enzyme-linked immunosorbent assay (ELISA) verification on the same sample set. 19 antigens verified by ELISA were processed to the validation stage with 60 T1D patients and 60 healthy controls. In the knowledge based approach, 126 pancreas enriched genes were selected from literature mining and bioinformatics analysis and measured for their sero-reactivity among 46 T1D patients and 46 healthy controls. 15 antigens were chosen for validation in 50 T1D patients and 50 healthy controls.

Kits for assessing the presence of antigens for type 1 diabetes are also contemplated. An exemplary kit includes an antigen selected from MLH1, MTIF3, PPIL2, NUP50, TOX4, FIGN, C9orf142, ZNF280D, HES1, QRFPR, CTRC, SNX6, SYTL4, ELA2A, IGRP, PAX6, and HMGN3 to test serological antibodies, as well as a suitable detection agent (e.g., a labeled secondary antibody).

EXAMPLE

Sera from T1D patients contain AAbs to human self-proteins. Thus, the sero-reactivity to 10,000 human proteins with sera from T1D patients and measured bound IgG. We scaled down the candidate number for validation in an independent sample set. In the knowledge based approach, we performed ELISA on 126 pancreas enriched genes and validate the candidates in an independent sample set. Taken together, 17 potential autoantigens were identified with sensitivities ranging from 10-27% at 95% specificity (Table 1).

Rapid antigenic protein in situ display (Rapid) ELISA was performed to confirm the sensitivities of autoantibodies biomakers. 96-well ELISA plates (Corning, ME) were coated with 10 ng/mL anti-glutathione S-transferase (GST) antibody (GE Healthcare, PA) in coating buffer (0.5 M carbonate bicarbonate buffer, pH 9.6) overnight at 4° C. On the next day, coated plates were washed 3 times with PBST and blocked with 5% milk-PBST (0.2% Tween) for 1.5 hrs at room temperature (RT).

Meanwhile, 40 ng/μL plasmids encoding candidate autoantigens were expressed in the human Hela cell-lysate based expression system at 30° C. for 1.5 hrs. After expression, candidate autoantigens were diluted in milk-PBST and captured in ELISA plates at 500 rpm for 1 h at RT. Plates were washed 5 times with PBST and incubated with diluted serum samples at 500 rpm for 1 h at RT. Then plates were washed again and incubated with HRP labeled anti-human secondary antibody (Jackson ImmunoResearch Laboratories, PA) for 1 h.

Finally, the plates were washed and incubated by 1-Step Ultra TMB—ELISA Substrate (Thermo scientific, IL) for detection and sulfuric acid to stop the reaction. OD450 was measured by Envision Multilabel Reader (Perkin Elmer, MA). Expression of candidate autoantigens was confirmed by mouse monoclonal anti-GST primary antibody and HRP labeled anti-mouse secondary antibody detection on the same plate. Relative absorbance was obtained by using the raw ELISA data dividing by the medium signal of each sample across all the antigens tested on the same day. The sensitivities for each antigen were determined at 95% specificity in comparison to a healthy control sample.

Prior work indicated that there are four known AAb biomarkers identified in T1D. The 5-year risk for T1D is 20-25% for subjects with one AAb, 50-60% for subjects with two AAbs, near 70% for subjects with three AAbs and 80% for those with four AAbs. Additional AAb biomarkers will help to improve the risk prediction in the general population. Thus, for example, the presence of autoantibodies to the antigen proteins as disclosed herein could be tested by immunoassays. The presence of one or more autoantibodies disclosed herein could be used as prediction of T1D onset.

The embodiments and example described above are not intended to be limiting.

TABLE 1

Discovery and Validation Statistics for 17 T1D biomarkers

| Antigen | Discovery | | Validation | | All | |
| --- | --- | --- | --- | --- | --- | --- |
| | Sensitivity | Specificity | Sensitivity | Specificity | Sensitivity | Specificity |
| MLH1 | 0.15 | 0.95 | 0.33 | 0.95 | 0.27 | 0.95 |
| MTIF3 | 0.15 | 0.95 | 0.20 | 0.95 | 0.25 | 0.95 |
| QRFPR | 0.13 | 0.95 | 0.06 | 0.95 | 0.20 | 0.95 |
| PPIL2 | 0.20 | 0.95 | 0.18 | 0.95 | 0.19 | 0.95 |
| NUP50 | 0.15 | 0.95 | 0.17 | 0.95 | 0.16 | 0.95 |
| CTRC | 0.17 | 0.95 | 0.08 | 0.95 | 0.15 | 0.95 |
| SNX6 | 0.13 | 0.95 | 0.04 | 0.95 | 0.15 | 0.95 |
| TOX4 | 0.20 | 0.95 | 0.12 | 0.95 | 0.13 | 0.95 |
| FIGN | 0.13 | 0.95 | 0.12 | 0.95 | 0.13 | 0.95 |
| SYTL4 | 0.20 | 0.95 | 0.02 | 0.95 | 0.13 | 0.95 |
| ELA2A | 0.11 | 0.95 | 0.04 | 0.95 | 0.13 | 0.95 |
| C9orf142 | 0.18 | 0.95 | 0.05 | 0.95 | 0.11 | 0.95 |
| ZNF280D | 0.13 | 0.95 | 0.08 | 0.95 | 0.11 | 0.95 |
| HES1 | 0.10 | 0.95 | 0.15 | 0.95 | 0.11 | 0.95 |
| IGRP | 0.17 | 0.95 | 0.02 | 0.95 | 0.11 | 0.95 |
| PAX6 | 0.15 | 0.95 | 0.08 | 0.95 | 0.11 | 0.95 |
| HMGN3 | 0.28 | 0.95 | 0.08 | 0.95 | 0.10 | 0.95 |

What is claimed is:

1. A method comprising:
contacting an antibody-containing fluid sample from a subject with proteins in a nucleic acid programmable protein array (NAPPA), wherein the NAPPA comprises proteins mutL homolog 1 (MLH1), mitochondrial translational initiation factor 3 (MTIF3), peptidylprolyl isomerase (cyclophilin)-like 2 (PPIL2), nucleoporin 50 (NUP50), detecting antibody binding to the NAPPA proteins with a suitable detection agent.

2. A method comprising:
contacting an antibody-containing fluid sample from a subject with proteins linked to a rapid antigenic protein in situ display enzyme linked immunosorbent assay (rapid ELISA) plate, wherein the proteins comprise mutL homolog 1 (MLH1), mitochondrial translational initiation factor 3 (MTIF3), peptidylprolyl isomerase (cyclophilin)-like 2 (PPIL2), and nucleoporin 50 (NUP50);
detecting antibody binding to the proteins with a suitable detection agent.

3. The method of claim 1, wherein the proteins further comprise tox high mobility group box family member 4 (TOX4), fidgetin (FIGN), paralog of XCRCC4 and XLF (PAXX), zinc finger protein 280D (ZNF280D), Hes family BHLH transcription factor 1 (HES1), pyroglutamylated RFamide peptide receptor (QRFPR), chymotrypsin C (CTRC), sorting nexin 6 (SNX6), synaptotagmin like 4 (SYTL4), elastase 2A (ELA2A), glucose-6-phosphatase-related protein (IGRP), paired box 6 (PAX6), and high mobility group nucleosomal binding domain 3 (HMGN3).

4. The method of claim 1, wherein the detection agent comprises a label.

5. The method of claim 2, wherein the proteins further comprise tox high mobility group box family member 4 (TOX4), fidgetin (FIGN), paralog of XCRCC4 and XLF (C9orf142), zinc finger protein 280D (ZNF280D), Hes family BHLH transcription factor 1 (HES1), pyroglutamylated RF-amide peptide receptor (QRFPR), chymotrypsin C (CTRC), sorting nexin 6 (SNX6), synaptotagmin like 4 (SYTL4), elastase 2A (ELA2A), glucose-6-phosphatase-related protein (IGRP), paired box 6 (PAX6), and high mobility group nucleosomal binding domain 3 (HMGN3).

6. The method of claim 2, wherein the detection agent comprises a label.

\* \* \* \* \*